United States Patent [19]

Cooper et al.

[11] Patent Number: 5,126,350
[45] Date of Patent: Jun. 30, 1992

[54] POLYCYCLIC AROMATIC ANTIFUNGAL COMPOUNDS

[75] Inventors: Raymond Cooper, Yardley, Pa.; Ann C. Horan, Summit, N.J.; Joseph A. Marquez, Montclair, N.J.; Mahesh G. Patel, Verona, N.J.

[73] Assignee: Schering Corporation, Kenilworth, N.J.

[21] Appl. No.: 537,383

[22] Filed: Jun. 13, 1990

[51] Int. Cl.$^5$ .................. A61K 31/435; C07D 491/16; A23K 1/17; C17P 17/18
[52] U.S. Cl. ..................... 514/279; 546/35; 546/34; 435/118; 435/252.64
[58] Field of Search ..................... 546/35, 34; 514/279

[56] References Cited

U.S. PATENT DOCUMENTS 4,551,538 11/1985 Lee et al. .............................. 546/35

FOREIGN PATENT DOCUMENTS 0156193 2/1985 European Pat. Off. .

OTHER PUBLICATIONS

Merck Index, 10th Edition 1983, pp. 32-33 (#199).

*Primary Examiner*—Cecilia Shen
*Attorney, Agent, or Firm*—Thomas D. Hoffman; Gerald S. Rosen

[57] ABSTRACT

A compound represented by the formula I:

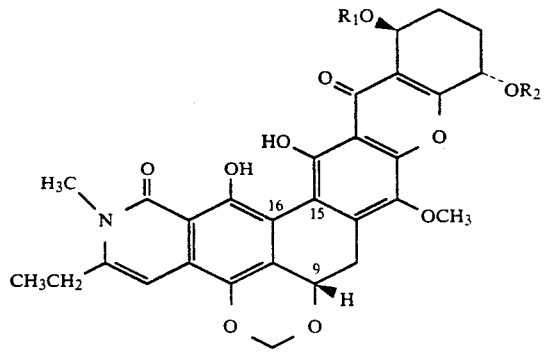

wherein $R_1$ and $R_2$ are independently hydrogen or ($C_2$-$C_{10}$) alkanoyl in substantially chemically pure form, and pharmaceutical compositions thereof are disclosed.

12 Claims, No Drawings

POLYCYCLIC AROMATIC ANTIFUNGAL COMPOUNDS

BACKGROUND OF THE INVENTION

This invention relates to novel polycyclic aromatic antifungal compounds belonging to the albofungin family of compounds. The antifungal compounds of this invention are isolated from an antifungal complex produced by fermentation under controlled conditions using a biologically pure culture of the microorganism Actinoplanes sp. SCC 1906, ATCC 53878.

Albofungin is an antifungal antibiotic produced by *Streptomyces albus* var fungistaticus see the Merck Index, 10th Edition, 1983 at pp. 32-33.

The antibacterial, antiparasitic albofungins designated LL-D42067α and LL-D42067β are disclosed in U.S. Pat. No. 4,551,533 and Eurpoean Patent Application 156-193.

The novel, antifungal compounds of the present invention exhibit selectively superior antifungal activity compared to LL-D42067α.

SUMMARY OF THE INVENTION

The present invention provides a compound represented by the formula 1:

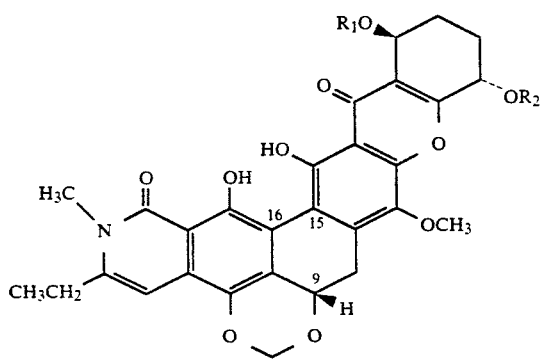

wherein $R_1$ and $R_2$ are independently hydrogen or ($C_2$-$C_{10}$) alkanoyl; in substantially chemically pure from, or a pharmaceutically acceptable salt thereof.

The present invention also provides a pharmaceutical composition comprising an antifungal effective amount of the compound of formula 1 and a pharmaceutically acceptable carrier or diluent.

The present invention also provides a method of eliciting an antifungal effect in a host having a susceptible fungal infection which comprises administering to said host an antifungal effective amount of the compound of formula 1 or a pharmaceutical composition thereof.

The present invention further provides a biologically pure culture of the microorganism Actinoplanes sp. SCC 1906 having the identifying characteristics of ATCC 53878, said culture being capable of producing the antifungal complex comprising a compound of formula 1 in a recoverable quantity upon fermentation, under aerobic conditions in an aqueous medium containing assimilable sources of nitrogen and carbon.

The present invention further provides an antifungal complex comprising a compound of claim produced by cultivating a strain of Actinoplanes sp. having the identifying characteristics of ATCC 53878 in a pH and temperature controlled aqueous nutrient medium containing assimilable sources of nitrogen and carbon, under controlled submerged aerobic conditions until a composition of matter having substantial antifungal activity is produced.

THE MICROORGANISM

The microorganism used for the production of the antifungal complex and the compounds of formula 1 is a biologically pure culture of Actinoplanes sp. SCC 1906, ATCC 53878. A viable culture of this microorganism has been deposited on Mar. 7, 1989 in the collection of the American Type Culture Collection (ATCC) in Rockville, Md. 20852, where it has been assigned accession number ATCC 53878. Should the deposited culture become lost, destroyed or non-viable during the longer of the thirty (30) year period from the date the culture was deposited or the five (5) year period after the last request for the deposited culture on the effective life of the patent which issues from this application, the culture will be replaced upon notice by applicants or assignee(s) of this application. Subcultures of Actinoplanes sp. SCC 1906, ATCC 53878 are available during the pendency of this application to one determined by the Commissioner of Patents and Trademarks to be entitled thereto under 37 CFR 1.14 and 35 USC C 122 and will be available to the public without restriction once a patent based on this application is granted. Use of the microorganism is dependent on the U.S. Patent Laws.

The microorganism was isolated from a sample of soil collected in Brazil and has been characterized and found to have the microscopic, macroscopic, and whole cell hydrolysis properties of the genus Actinoplanes.

DESCRIPTION OF ANTINOPLANES SP. SCC 1906. ATCC 53878

Source material for the following taxonomic evaluations was a frozen preparation of a pure culture of Actinoplanes sp. SCC 1906, ATCC 53878. Inoculum for the biochemical and physiological tests was prepared according to the procedures of Horan and Brodsky [Horan and Brodsky, *Int. J. Syst. Bacteriol.*, Vol. 32, pp. 195-200 (1982)].

The producing strain of the microorganism, SCC 1906, of this invention is a gram positive, filamentous organism. Microscopic observation reveals no aerial mycelia; the substrate mycelia are well developed and branching, approximately 0.4 to 0.9 microns in diameter and bear sporangia which are produced on distinct sporangiophores. The sporangia are globose with an irregular or asymmetric surface and are approximately 7 to 11 microns in diameter. Mature sporangia contain round zoospores, 1.1 to 1.5 microns in diameter. The zoospores become motile after contact with water.

Macroscopically, SCC 1906 grows well on most rich organic media forming yellow-brown to light orange vegetative mycelial pigments and yellow to yellow-brown diffusible pigments. Whole cell hydrolysates contain meso-diaminopimelic acid, galactose, glucose, mannose, arabinose, xylose, ribose, madurose and a trace of rhamnose. The producing culture, SCC 1906, is characterized as an member of the genus Actinoplanes.

Fermentation of the Microorganism

The antifungal complex of this invention is produced when the elaborating microorganism, Actinoplanes sp. SCC 1906, is grown in an aqueous nutrient medium under submerged aerobicc conditions at a temperture of about 27° C. to 40° C., preferably at from 27° C. to 35° C., and at a pH of from about 6.5 to 8.0 with agitation until substantial antibiotic activity is imparted to the medium. Temperature studies indicated that the organism grows rapidly at about 30° C. Therefore, the fermentation is preferably conducted employing a single temperature pattern of 30° C. for a period of about 24 to 96 hours. The fermentation is generally conducted from about 3 to 7 days, preferably for about 4 days. To determine when peak antibiotic production has been reached, samples of the medium are assayed every 24 hours for antibiotic content by bioassay of the whole broth against *Candida albicans Wisconsin*. The growth of the organism (packed cell volume), pH and dissolved oxygen levels were determined either intermittantly or continuously.

As nutrient medium, there is employed any suitable medium containing a source of carbon, for example an assimilable carbohydrate, and a source of nitrogen, for example an assimilable nitrogenous or proteinaceous material.

The medium employed for the fermentation contains amino acids and corn starch as the major sources of nitrogen and carbon, respectively. Under these conditions, the microoganism produces the antifungal complex of this invention containing at least 3 biologically active components (represented by formula 1) as determined by bioautography against both *C. albicans Wisconsin* of the antifungal complex after development of a thin layer chromatograph plate in 2:2:1 (v/v/v) chlorofrom: methanol: pH 3.5 acetate buffer.

The foregoing media are exemplary of the nutrients utilized by Actinoplanes sp. SCC 1906 to produce the antifungal/antibiotic complex of this invention. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from about 6.5 to 8.0, a pH of from about 6.5 to 7.5 being preferred. Prior to sterilization, the pH of the medium is usually adjusted to about 7.5 and prior to inoculation the pH is usually about 6.7.

The fermentation was initiated by the addition of the inoculum to the sterilized fermentation medium.

Generally, inoculum volume is 5% of total medium volume. The inoculum is prepared by addition of a sample of the frozen whole broth to an appropriate germination medium. A particularly preferred germination medium comprises 0.3% (w/v) of beef extract, 0.5% of tryptone; 0.5% of yeast extract; 0.1% of cerelose; 2.4% of potato starch; 0.2% of $CaCO_3$. The pH medium of the germination medium is not adjusted. There are usually two inoculum stages each lasting for 2 days at 30° C.

The fermentation medium is made up of 0.3% (w/v) of PD-650 dextrin, 10 mL of dark molasses; 0.5% (w/v) of soluble starch and 0.0.2 mL/L of antifoam. The pH of the fermentation medium is adjusted to 7.5 prior to sterilization. The fermentation stage usually requires from 24 to 120 hours with 4 days preferred and is generally conducted at about 30° C.

ISOLATION AND PURIFICATION OF ANTIFUNGAL COMPLEX AND THE COMPOUNDS OF THIS INVENTION

The antifungal complex of this invention is produced when the elaborating organism, Actinoplanes sp, SCC 1906 having the identifying characteristics of ATCC 53656 is grown in the appropriate nutrient medium.

The antifungal complex of this invention contains at least three (one major and two minor) biologically active components represented by formula 1. The antifungal complex containing the three components is separated from the filtered fermentation broth by solvent extraction of the broth with ethyl acetate at a pH value of 2.0. The compounds of this invention were isolated by from the complex by chromatography on CHP20P (using 0 to 100% $CH_3CN$ in as elvant), followed by Sephadex LH-20 (eluting with $CH_3OH$) and thereafter with CHP20P (using 0 to 100% acetone as elant). The three biologically active compounds of formula 1 wherein $R_1 = R_2 = H$; $R_1 = H$,

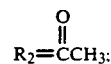

and $R_2 = H$ and

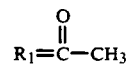

were separated as chemically pure compounds by HPLC on a YMC C-8 column using $CH_3CN$—$H_2O$ containing acetic acid as the mobile phase.

Using this procedure, 38 mg of the compound represented by formula 1 wherein $R_1 = R_2 = H$ and 10 mg of the minor components $R_1 = H$;

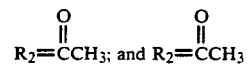

and $R_1 = H$ were isolated from a 60 L fermentation broth.

The physiochemical data for the compounds of this invention are given in Tables I–III.

TABLE I

Physico-Chemical Properties of Compound of Formula 1 ($R_1 = R_2 = H$)

$[\alpha]_D^{26} = +681°$ (C.), 0.5, DMF)

UV$\lambda$ max (MeoH)nn: 214 (e = 1.66), 255(e = 1.817), 319 (e = 0.6604), 381 (e = 1.156), 396(e = 1.297)

FAB Mass Spec. Data: 550 amu, MH+ m/z; Calc: 550.1692; found 550.1713 ($\Delta$4 ppm)

Molecular Formula: $C_{29}H_{28}NO_{10}$ $^1$H NMR$\delta$ (DMSO-d) 1.26[t, (7)3], 1.74 (br, 2), 1.95[tr, (14, 14)],2.2[tr, 1, 14, 14], 2.5, [dd, (13, 13) 1], 2.82, [q (7) 2], 3.5, (s, 3), 3.5, [dd, (5, 13) 1], 3.85, (s, 3), 4,51 (br, 1), 4.80 [br, (6, 3) 1], 4.85, [dd, (5, 13) 1], 4.95 (br, 1), 5.40, [d, (6) 1], 5.60, [d, (6) 1], 5.90(d, 5), 6.7 (s, 1), 13.2 (s, 1) 13.5 (s, 1).

$^{13}$C-NMR$\delta$ (DMSO-d$_6$) 11.5/24.8, 25.0, 25.2, 28.5, 29.4, 57.9, 61.0, 62.5, 71.0, 91.0, 97.3, 108.2, 109.2, 110.6, 113.2, 118.5, 125.2, 126.2, 134.5, 134.7, 135.5, 145.4, 147.4, 150.6, 151.9, 164.8, 165.1, 182.0;

TABLE II

Physico-Chemical Properties of the Compound of 1

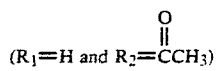

($R_1$=H and $R_2$=ĊCH$_3$)

FAB-Mass Spectral Data: 592 amu (MH+) m/z; Calc: 592,1815; found 592,1811 532 (MH+-ACOH) m/z; Calc 532.160; found 532.1607

$^1$H-NMR$\delta$ (DMSO-d$_6$) 1.26[t, (7) 3] 1.8–1.95(m), 2.0 (s,3), 2.5(m) 2.82 (q (7) 2), 3.5 (s, 3), 3.5(m), 3.87 (s, 3), 4.5 (m, 1), 4.85(m), 5.15 (s, O—H) 5.40 (d (6) 1) 5.60 (d, (6) 1) 5.95 (brs, 1), 6.7 (s, 1)

TABLE III

Physico-Chemical Properties of Compound of Formula I

($R_1$=ĊCH$_3$, $R_2$=H)

FAB-Mass Spectral Data: 592 amu (MH+) m/z; Calc: 592.1815; Found 592.1811.

$^1$H-NMRS (DMSO-d$_6$): 1.26[t, (7)], 1.8–1.95(m), 2.1 (s, 3), 2.5(m) 2.82[q (7) 2], 3.5 (s, 3), 3.5(m), 3.85 (s,3), 4.65 (m.1), 4,85 [dd (5,13)], 5.40 [d, (6) 1], 5.60 [(6) 1], 6.1 (d), 6.7 [s, 1].

STRUCTURAL DETERMINATION

The physicolchemical data (and circular dichroism studies) of the compounds of this invention were compared side by side with the physiochemical data obtained from authentic samples of albofungin and LL-D42067$\alpha$ and LL-D42067$\beta$. Based on these comparative physiochemical data, the structure of the compounds of this invention were determined to be consistent with that represented by formula 1.

BIOLOGICAL ACTIVITY OF THE ANTIFUNGAL COMPLEX AND COMPOUNDS OF THIS INVENTION

The antifungal complex and compounds of this invention exhibit biological activity against gram positive bacteria, yeast, fungi and dermatophytes, which is statistically selectively superior to that of LL-D42067$\alpha$.

TABLE IV

Comparative Antifungal Activity of The Compound of Formula I ($R_1$ = $R_2$ = H) and LL-D42067$\alpha$

| Microorganism | Formula 1. $R_1$ = $R_2$ = H Geometric Mean Minimum Inhibitory Concentration (mcg/ml) | LL-D42067$\alpha$ |
|---|---|---|
| Yeast (SDB)[1] 12 species | <0.125 | 0.125 |
| Yeast (EMEM)[2] 9 species | <0.125 | 32 |
| Dermatophyles (SDB)[1] 9 species | <0.125 | 0.5 |

[1]SDB = Sabouraud Dextrose Broth, pH 5.7
[2]EMEM = Eagles Minimum Essential Medium, pH 7.0

PHARMACEUTICAL COMPOSITIONS

This invention also contemplates antifungal effective pharmaceutical compositions comprising an antifungal effective amount of a compound of formula 1 or pharmaceutically acceptable salts thereof in admixture with a pharmaceutically acceptable, non-toxic carrier adapted for topical, oral or parenteral use.

The preferred pharmaceutically acceptable salts are nontoxic acid addition salts formed by adding to the compounds of the present invention about a stoichiometric amount of a mineral acid, such as HCl, HBr, H$_2$SO$_4$ or H$_3$PO$_4$, or of an organic acid, such as acetic, propioni, valeric, oleic, palmitic, stearic, lauric, benzoi, lactic, paratoluenesulfonic, methanesulfonic, citric, maleic, fumaric, sucinic and the like.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 0.1 to 10 grams of a compound of formula 1 per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously ar usually in the form of a sterile solution, and may contain salts or glucose to make the solution isotonic.

In general, the dosage of compound of formula 1 administered to combat a given microbial infection is similar to the dosage requirements of the present commercial products miconazole, clotrimazole, and ketoconazole.

In general, the topical dosage range of the compound of formula 1 is from about 0.1% to about 10% by weight of a particular pharmaceutical composition formulated in single or divided dosae, with the preferred range being about 0.5% to about 4% and with the most preferred range being about 1% to about 2%.

In general, the oral dosage for humans of the compound of formula 1 adiministered to combat a given microbial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula 1 administered to combat a given microbial infection ranges from about 0.1 mg per kilogram of body weight per day, to about 20 mg per kilogram of body weight per day in single or divided dosage, with about 1 mg per kilogram of body weight per day being preferred.

It will be appreciated that the actual preferred dosages of the compound of this invention or pharmaceutically acceptable salts thereof will vary according to the particular composition formulated, the mode of application and the particular situs, host and disease being treated. Many factors that modify the action of the drug will be taken into account by the attending clinician, e.g. age, body weight, sex, diet, time administration, rate of excertion, condition of the host, drug combinations, reaction sensitivities and severity of the disease. Administration can be carried out continuously or periodically within the maximum tolerated dose. Optimal applicaiton rates for a given set of conditions can be readily ascertained by the attending clinician using conventional dosage determination tests.

The following examples illustrate the invention:

EXAMPLE 1

Preparation of the Antifungal Complex of This Invention

A. Inoculum Preparation

1) Initial Stage

Prepare a 250 mL Erlemneyer flask with 70 mL of the following germination medium:

| | |
|---|---|
| Beef Extract | 3 g |
| Tryptone | 5 g |
| Yeast Extract | 5 g |
| Cerelose | 1 g |
| Potato Starch | 24 g |
| Calcium Carbonate | 2 g |
| Tap Water | 1000 mL |
| AF-1* | 1 mL |

*AF-1 is an antifoam agent available from Dow Corning Corp., Midland, MI 48641.

Adjust the pH of the germination broth to 7.5. Sterilize the broth and after cooling, add 3.5 mL of a frozen whole broth sample of the microorganism of this invention from a previously prepared inoculum to each flask broth. Incubate at 30° C. with continual agitation at 300 rpm for 48 hours.

2) Second Stage

Transfer 25 mL of the first stage germination broth to each of twenty 2-liter Erlenmeyer flasks, each containing 500 mL of the same germination medium and which had been previously pH adjusted and sterilized.

Incubate at 30° C. with continual agitation at 300 rpm for 48 hours.

B. Fermentation

Into a 10 L fermenter containing in milliliters/L or grams/L: PD-650 dextrin, 3.0; dark molasses, 10 mL/L; soluble starch, 5.0; and antifoam 0.2 mL/L, add 500 ml of the second stage germination. The pH of the fermentation was adjusted to 7.5 prior to sterilization.

Incubate the fermentation broth at 30° C. at an air flow of 3.5 L/minute with continual agitation at 300 rpm for 96 hours. Evaluate antibiotic production by disc assay of an aliquot of the broth against *Candida albicans* Wisconsin.

The material used for isolation and structure elucidation of the compounds of this invention were isolated from six 10 L fermentations.

The whole broth (60 liters) was filtered. The filtrate was adjusted to pH 2 and extracted two times with 60 liters of ethyl acetate. The extracts were pooled, concentrated to dryness and precipitated as yellow complex. The resulting yellow complex was further purified by chromatography on Sephadex LH-20 and CHP20P gel column to provide 8 mg of a substantially chemically pure compound as yellow solid of formula 1 where $R_1=R_2=H$ as the major component and two minor components which were further separated into substantially chemically pure pure compounds by preparative thin layer chromatography on silica gel plates. After removal of solvents there was obtained two yellow amorphous solids: 0.5 mg of a compound having the structural formula 1 where $R_1=H$

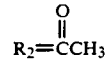

and 1.0 mg of a compound having the structural formula I wherein $R_2=H$ and

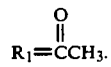

The term "substantially chemically pure" as used herein in the specification and claims in reference to the compounds represented by formula 1 means the compounds are homogeneous (i.e. a single component) by standard analytical chromatographic techniques.

What is claimed is:

1. A compound represented by the formula 1:

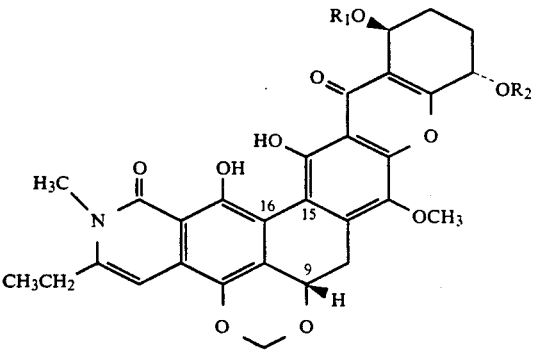

wherein one of $R_1$ or $R_2$ is hydrogen and the other of $R_1$ or $R_2$ is ($C_2$-$C$-10) alkanoyl in substantially chemically pure form, or a pharmaceutically acceptable salt thereof.

2. A compound represented by the formula 1:

in substantially chemically pure form, or a pharmaceutically acceptable salt thereof.

3. A compound of claim 1 wherein $R_1$ is hydrogen.

4. A compound of claim 1 wherein $R_2$ is hydrogen.

5. A pharmaceutical composition comprising an antifungal effective amount of the compound of claim 2 and a pharmaceutically acceptable carrier or diluent.

6. A pharmaceutical composition of claim 5 suitable for parenteral administration.

7. A pharmaceutical composition of claim 5 suitable for topical administration.

8. A pharmaceutical composition of claim 5 suitable for oral administration.

9. A method of eliciting an antifungal effect in a host having a susceptible fungal infection which comprises administering to said host an antimicrobially effective amount of the compound of claim 2 or a pharmaceutical composition thereof.

10. A method of claim 9 wherin the route of administration is parenteral.

11. A method of claim 9 wherein the route of administration is topical.

12. A method of claim 9 wherein the route of administration is oral.

* * * * *